(12) United States Patent
Li et al.

(10) Patent No.: US 10,809,252 B2
(45) Date of Patent: Oct. 20, 2020

(54) TIME-RESOLVED FLUORESCENT IMMUNOCHROMATOGRAPHIC ASSAY RAPID TEST KIT FOR TYPE I PYRETHROID

(71) Applicant: OILCROPS RESEARCH INSTITUTE OF CHINESE ACADAMY OF AGRICULTURE SCIENCES, Hubei (CN)

(72) Inventors: Peiwu Li, Hubei (CN); Qi Zhang, Hubei (CN); Xiaoqian Tang, Hubei (CN); Hui Li, Hubei (CN); Jun Jiang, Hubei (CN)

(73) Assignee: OILCROPS RESEARCH INSTITUTE OF CHINESE ACADAMY OF AGRICULTURE SCIENCES, Hubei (CN)

( * ) Notice: Subject to any disclaimer, the term of this patent is extended or adjusted under 35 U.S.C. 154(b) by 209 days.

(21) Appl. No.: 15/905,829

(22) Filed: Feb. 27, 2018

(65) Prior Publication Data

US 2018/0246086 A1    Aug. 30, 2018

(30) Foreign Application Priority Data

Feb. 27, 2017 (CN) .......................... 2017 1 0107589

(51) Int. Cl.
*G01N 33/543* (2006.01)
*G01N 33/533* (2006.01)

(52) U.S. Cl.
CPC ..... *G01N 33/54306* (2013.01); *G01N 33/533* (2013.01); *G01N 33/54386* (2013.01); *G01N 2430/12* (2013.01)

(58) Field of Classification Search
CPC ............. G01N 2430/12; G01N 33/533; G01N 33/54306; G01N 33/54386
See application file for complete search history.

(56) References Cited

FOREIGN PATENT DOCUMENTS

| CN | 103278631 | | 9/2013 |
|---|---|---|---|
| CN | 106701689 A | * | 5/2017 |

OTHER PUBLICATIONS

English machine translation of CN 106701689 A, published May 24, 2017.*
Wang Heng-Ling, et al., "Preparation and application of etofenprox pesticides artificial antigen," Chinese Journal of Oil Crop Sciences, vol. 35, Oct. 2013, pp. 1-6.

* cited by examiner

*Primary Examiner* — Galina M. Yakovleva
(74) *Attorney, Agent, or Firm* — JCIPRNET

(57) ABSTRACT

The present invention relates to a time-resolved fluorescent immunochromatographic assay rapid test kit for quantitative determination of the level of type I pyrethroid, which has the advantages of simple operation, rapid detection, and with high accuracy. The kit has a quantitative detection limit of 9.12 ng/mL for a type I pyrethroid sample. When the kit is applied to the detection of an actual sample of type I pyrethroid and by comparing the detection result obtained by HPLC, the kit has a coefficient of correlation of 0.986 ($R^2$). Hence, the kit is applicable to the detection by using the actual samples of type I pyrethroid.

10 Claims, 1 Drawing Sheet
Specification includes a Sequence Listing.

SEQUENCE LISTING

<160> NUMBER OF SEQ ID NOS: 8

<210> SEQ ID NO 1
<211> LENGTH: 363
<212> TYPE: DNA
<213> ORGANISM: Mice

<400> SEQUENCE: 1

```
caggttactt tgaaagagtc tggccctggg atattgcagc cctcccagac cctcagtctg    60
acttgttctt tctctgggtt ttcactgagc acttatggta taggaatagg ctggattcgt   120
cagtcttcag ggaggggtct ggagtggctg gcacacattt ggtggaatga ataggtac    180 tataacatag ccctgaagag ccggctcaca atctccaagg atgcctccaa caaccagttt   240
ttcctcaagc tcgccagtgt ggacactgca gatattgcca cgtactactg tgttcgcggc   300
tacggccgcc ccttctatgc tatggactac tggggtcaag gaaccacagt caccgtctcc   360
tca                                                                 363
```

<210> SEQ ID NO 2
<211> LENGTH: 327
<212> TYPE: DNA
<213> ORGANISM: Mice

<400> SEQUENCE: 2

```
caggctgttg tgactcagga atctgcactc accacatcac ctggtgaaac agtcacactc    60
acttgtcgct caagtactgg ggctgttaca actagtaact atgtcaactg gtccaagaa   120 aaaccagatc atttattcac tggtctaata ggtggtacca caaccgagg tccaggtgtt   180 cctgccagat tctcaggctc cctgattgga gacaaggctg ccctcaccat cactgggaca   240
cagactgagg atgaggcaat atatttctgt gctctatggt acagcaacca ttgggtgttc   300
ggtggaggaa ccaaactgac tgtccta                                       327
```

<210> SEQ ID NO 3
<211> LENGTH: 121
<212> TYPE: PRT
<213> ORGANISM: Mice

<400> SEQUENCE: 3

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Ile Gly Trp Ile Arg Gln Ser Ser Gly Arg Gly Leu Glu
        35                  40                  45

Trp Leu Ala His Ile Trp Trp Asn Asp Asn Arg Tyr Tyr Asn Ile Ala
    50                  55                  60

Leu Lys Ser Arg Leu Thr Ile Ser Lys Asp Ala Ser Asn Asn Gln Phe
65                  70                  75                  80

Phe Leu Lys Leu Ala Ser Val Asp Thr Ala Asp Ile Ala Thr Tyr Tyr
                85                  90                  95

Cys Val Arg Gly Tyr Gly Arg Pro Phe Tyr Ala Met Asp Tyr Trp Gly
            100                 105                 110

Gln Gly Thr Thr Val Thr Val Ser Ser
        115                 120
```

<210> SEQ ID NO 4
<211> LENGTH: 109
<212> TYPE: PRT
<213> ORGANISM: Mice

<400> SEQUENCE: 4

```
Gln Ala Val Val Thr Gln Glu Ser Ala Leu Thr Thr Ser Pro Gly Glu
1               5                   10                  15
```

```
Thr Val Thr Leu Thr Cys Arg Ser Ser Thr Gly Ala Val Thr Thr Ser
            20                  25                  30

Asn Tyr Val Asn Trp Val Gln Glu Lys Pro Asp His Leu Phe Thr Gly
            35                  40                  45

Leu Ile Gly Gly Thr Asn Asn Arg Gly Pro Gly Val Pro Ala Arg Phe
 50                  55                  60

Ser Gly Ser Leu Ile Gly Asp Lys Ala Ala Leu Thr Ile Thr Gly Thr
65                   70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 5
<211> LENGTH: 31
<212> TYPE: DNA
<213> ORGANISM: Artificial Sequence
<220> FEATURE:
<223> OTHER INFORMATION: forward primer for heavy chain variable region

<400> SEQUENCE: 5
aagcagtggt atcaacgcag agtacatggg g                                 31

<210> SEQ ID NO 6
<211> LENGTH: 21
<212> TYPE: DNA
<213> ORGANISM: Artificial Sequence
<220> FEATURE:
<223> OTHER INFORMATION: reverse primer for heavy chain variable region

<400> SEQUENCE: 6
caggggccag tggatagaca g                                            21

<210> SEQ ID NO 7
<211> LENGTH: 30
<212> TYPE: DNA
<213> ORGANISM: Artificial Sequence
<220> FEATURE:
<223> OTHER INFORMATION: forward primer for light chain variable region

<400> SEQUENCE: 7
gcagtggtat caacgcagag tacatggggg                                   30

<210> SEQ ID NO 8
<211> LENGTH: 22
<212> TYPE: DNA
<213> ORGANISM: Artificial Sequence
<220> FEATURE:
<223> OTHER INFORMATION: reverse primer for light chain variable region

<400> SEQUENCE: 8
ctaagcctga ctgatggcga ag                                           22
```

TIME-RESOLVED FLUORESCENT IMMUNOCHROMATOGRAPHIC ASSAY RAPID TEST KIT FOR TYPE I PYRETHROID

CROSS-REFERENCE TO RELATED APPLICATION

This application claims the priority benefit of China application serial no. 201710107589.9, filed on Feb. 27, 2017. The entirety of the above-mentioned patent application is hereby incorporated by reference herein and made a part of this specification.

BACKGROUND OF THE INVENTION

1. Field of the Invention

The present invention relates to the field of pesticide detection and in particular to a time-resolved fluorescent immunochromatographic assay rapid test kit for type I pyrethroid.

2. Description of Related Art

Type I pyrethroid mainly includes permethrin, phenothrin, bio-resmethrin, bifenthrin, etc., and is widely used in the control of diseases and pests on fruits, vegetables and crops such as rice. Long-term use of type I pyrethroid in large quantity causes the pests to produce resistance, and pose a certain threat to the environmental and human safety. The limit is between 0.02 ppm and 10 ppm. For example, China's national standard stipulates that the maximum residue limit (MRL) of etofenprox in vegetables is 1 ppm, and the MRL of etofenprox in tea is 10 ppm; and the MRLs of permethrin in vegetables and fruits are 1 ppm and 2 ppm, respectively.

The existing detection methods mainly include instrumental analysis and immunoassay. Immunoassay is an analytical method based on the specific recognition and reversible binding reaction of antigens to antibodies. Immunoassay method has high selectivity and sensitivity. Compared with the instrumental analysis, immunoassay method greatly shortens the sample processing time and reduces the detection cost. Time-resolved fluorescent immunochromatographic assay (TRFICA) is a method in which 190 nm europium ($Eu^{3+}$) is used as a high-affinity probe to prepare time-resolved fluorescent immunochromatographic test strips, and having the advantages of high sensitivity, stable property, with no interference of fluorescent background, short detection time (only 6-8 min for general detection) and others. It is very suitable for being developed as a method for rapid detection of pesticide residues.

SUMMARY OF THE INVENTION

In view of the above problems, the present invention provides a time-resolved fluorescent immunochromatographic assay rapid test kit for type I pyrethroid.

Time-resolved fluorescent immunochromatographic assay rapid test kit for type I pyrethroid comprises a fluorescent test strip, and a sample reaction vial containing a lyophilized product of a europium-labelled universal monoclonal antibody against type I pyrethroid. The fluorescent test strip comprises a cardboard, the cardboard comprises a plurality of adjacent pads comprising an absorbent pad, a detection pad, and a sample pad adhered in sequence from top to bottom on one side of the cardboard, in which each of the adjacent pads are connected at an overlapped junction of the adjacent pads. The detection pad comprises a nitrocellulose membrane as a base pad, and transverse quality control line and detection line are arranged from top to bottom on the nitrocellulose membrane. The quality control line is coated with rabbit anti-mouse polyclonal antibody, and the detection line is coated with a complete antigen (hapten-1-OVA) of type I pyrethroid.

The universal monoclonal antibody against type I pyrethroid is secreted by the hybridoma cell line QW8#, deposited on Aug. 30, 2016 to China Center for Type Culture Collection (CCTCC) (Wuhan University, Wuhan, China) under CCTCC Accession No. of C2016164.

In accordance with the above solution, the complete antigen (hapten-1-OVA) of type I pyrethroid comprises a structural formula of

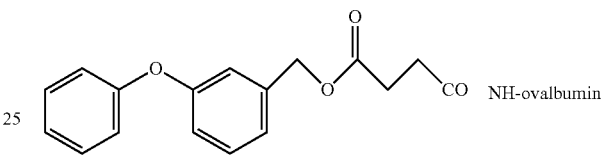

and is obtained specifically by reacting 3-phenoxybenzyl alcohol and succinic anhydride to generate 4-oxo-4-(3-phenoxybenzyloxy) butyric acid, a universal hapten of type I pyrethroid, and then coupling the ovalbumin (OVA) to the hapten by active ester method. The reaction equation is shown in FIG. 1.

In accordance with the above solution, the europium-labelled universal monoclonal antibody against type I pyrethroid is prepared through a process comprising: dialyzing the universal monoclonal antibody against type I pyrethroid in a carbonate buffer solution, mixing fully with a europium labelling reagent at a weight ratio of 0.5-2:1, allowing the mixture to stand overnight, and then separating the europium-labelled universal monoclonal antibody against type I pyrethroid by chromatography using G-50 column (for example, SEPHADEX® G-50 chromatographic column), followed by elution, and collection of targeted product.

In accordance with the above solution, in the fluorescent test strip, the absorbent pad is 15-20 mm long and 3-4 mm wide; the detection pad is 25-30 mm long and 3-4 mm wide; the sample pad is 12-18 mm long and 3-4 mm wide; and the overlapped junction of the plurality of adjacent pads is 1-3 mm.

In accordance with the above solution, the detection line on the detection pad in the fluorescent test strip is 15-20 mm away from a top edge of the nitrocellulose membrane; the distance between the quality control line and the detection line is 5-10 mm; and the sample reaction vial is a 1-5 mL bayonet vial.

In accordance with the above solution, the complete antigen of type I pyrethroid is coated in an amount of 480-1000 ng/cm on the detection line of the detection pad in the fluorescent test strip; the rabbit anti-mouse polyclonal antibody is coated in an amount of 100-900 ng/cm on the quality control line; and the content of the lyophilized product of the europium-labelled universal monoclonal antibody against type I pyrethroid in the sample reaction vial is 0.2-1.0 μg.

In accordance with the above solution, the fluorescent test strip is obtained through a process comprising steps of:

(1) cutting an absorbent paper to obtain the absorbent pad;

(2) preparation of the detection pad, comprising:

formulating a coating solution of the complete antigen (hapten-1-OVA) of type I pyrethroid into a concentration of 0.2-1.0 mg/mL, coating transversely on a nitrocellulose membrane by means of line spray to obtain the detection line, and then drying for 30-60 min at 37-40° C.; and formulating a coating solution of the rabbit anti-mouse polyclonal antibody into a concentration of 0.10-0.80 mg/mL, coating transversely on the nitrocellulose membrane by means of line spray to obtain the quality control line, and then drying for 30-60 min at 37-40° C.;

(3) preparation of the sample pad, comprising soaking a glass fiber membrane in a blocking solution, taking out, and drying for 3-6 hours at 37-40° C., to obtain the sample pad, which is then stored in a desiccator at room temperature; and (4) assembly of the fluorescent test strip, comprising adhering the plurality of adjacent pads comprising the absorbent pad, the detection pad, and the sample pad from top to bottom on one side of the cardboard, wherein each of the plurality of adjacent pads are connected at the overlapped junction of the plurality of adjacent pads to obtain the fluorescent test strip.

In accordance with the above solution, in the preparation of the fluorescent test strip, the coating solution of the complete antigen (hapten-1-OVA) of type I pyrethroid is formulated in a coating buffer comprising 0.1 g bovine serum albumin, 0.002 g sodium azide, 0.08 g sodium chloride, 0.029 g disodium hydrogen phosphate dodecahydrate, 0.002 g potassium chloride, and 0.002 g potassium dihydrogen phosphate per 10 mL.

In accordance with the above solution, in the preparation of the fluorescent test strip, the coating solution of the rabbit anti-mouse polyclonal antibody is formulated in a coating buffer comprising 0.002 g sodium azide, 0.08 g sodium chloride, 0.029 g disodium hydrogen phosphate dodecahydrate, 0.002 g potassium chloride, and 0.002 g potassium dihydrogen phosphate per 10 mL.

In accordance with the above solution, the blocking solution used in the preparation of the fluorescent test strip comprises 0.5-2 g ovalbumin, 2 g sucrose, 0.02 g sodium azide, 0.8 g sodium chloride, 0.29 g disodium hydrogen phosphate dodecahydrate, 0.02 g potassium chloride, and 0.02 g potassium dihydrogen phosphate per 100 mL.

In accordance with the above solution, the time-resolved fluorescent immunochromatographic assay rapid test kit for type I pyrethroid further comprises a sample diluent, and a sample dilution pipette, where the sample diluent is a solution with 0.01-0.30% (vol/vol) of TWEEN®20 (polyoxyethylene (20) sorbitan monolaurate) in water.

The present invention further provides use of the time-resolved fluorescent immunochromatographic assay rapid test kit for type I pyrethroid in the determination of the level of type I pyrethroid, comprising adding a sample solution to be tested to the sample reaction vial, mixing fully, inserting the fluorescent test strip, reacting for 6 min at 37° C., and assaying by using a time-resolved fluorescent immunochromatographic assay instrument, to obtain a ratio of a fluorescence intensity value of the detection line (T) to a fluorescence intensity value of the quality control line (C) on the fluorescent test strip (T/C); and obtaining the level of type I pyrethroid in the sample solution to be tested, according to a relation curve of the ratio of the fluorescence intensity of the detection line (T) to the fluorescence intensity of the quality control line (C) on the fluorescent test strip (T/C) against the concentration of type I pyrethroid.

In accordance with the above solution, the relation curve of the ratio of the fluorescence intensity of the detection line (T) to the fluorescence intensity of the quality control line (C) on the fluorescent test strip (T/C) against the concentration of type I pyrethroid is obtained through a method comprising:

(1) formulating a standard solution comprising a series of concentrations of type I pyrethroid;

(2) adding a suitable amount of the standard solution comprising the series of concentrations of type I pyrethroid respectively to a sample reaction vial, mixing fully, inserting the fluorescent test strip, reacting for 6 min at 37° C., assaying by using a time-resolved fluorescent immunochromatographic assay instrument, to obtain fluorescence intensity values of the detection line (T) and the quality control line (C) on each of the fluorescent test strips, and obtaining a ratio of the fluorescence intensity values of the detection line (T) and the quality control line (C) on each of the fluorescent test strips (T/C); and (3) fitting to obtain the relation curve of the ratio of the fluorescence intensity of the detection line (T) to the fluorescence intensity of the quality control line (C) on the fluorescent test strip (T/C) against the concentration of type I pyrethroid.

In this study, a universal monoclonal antibody against type I pyrethroid is coupled with a europium labelling reagent to develop a highly sensitive time-resolved fluorescent immunochromatographic test strip for quantitative determination of type I pyrethroid by using a time-resolved fluorescent immunochromatographic assay instrument. In this way, a highly sensitive and rapid time-resolved fluorescent immunochromatographic method for detecting type I pyrethroid is established.

The present invention has the following advantageous effects.

The time-resolved fluorescent immunochromatographic assay rapid test kit for type I pyrethroid provided in the present invention is applicable to the quantitative detection of the level of type I pyrethroid, and has the advantages of simple operation, rapid detection, and with high accuracy.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
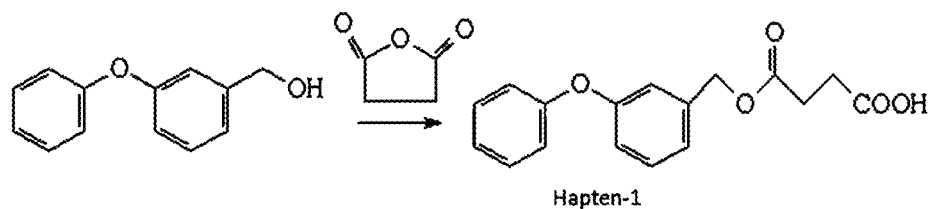
FIG. 1 is a schematic diagram showing the reaction of antigen synthesis in the present invention.

Example 1. Production of Universal Monoclonal Antibody Against Type I Pyrethroid Screening of Hybridoma Cell Line QW8#
1. Synthesis of Antigen and Immunization of Animals Commercially available 3-phenoxybenzyl alcohol standard was purchased for synthesizing a complete antigen. The specific synthesis steps were as follows. 4 mg of 3-phenoxybenzyl alcohol was dissolved in 2 mL of chloroform, and 50 µl of succinic anhydride was added. The mixture was stirred and reacted overnight at room temperature. The product was evaporated to dryness and extracted twice with ethyl acetate to give an organic layer which was rotary evaporated to give the product Hapten-1 (FIG. 1).

1.0 mg of Hapten-1 was dissolved in 800 µL of DMF, and then 0.2 mmol of DCC and 0.3 mmol of NHS were respectively added, and stirred and reacted overnight. The mixture was added dropwise to 4 mL of a 10 mg/mL BSA solution and reacted for 4 hours at room temperature. 3-phenoxybenzyl alcohol and excess of Hapten-1 were removed by dialysis for 3 days in PBS (phosphate buffer solution, pH 7.4) at 4° C. Finally, identification by conventional UV scanning showed that Hapten-1-BSA, a general complete antigen of type I pyrethroid was prepared, and used as immunogen.

The same batch of 6 to 8-week old BALB/c female mice were purchased and numbered. The mice were housed for several days to preclude the presence of abnormalities, and immunized with the synthetic complete antigen Hapten-1-BSA at a dosage of 100 µg/animal. Upon the primary immunization, the synthetic complete antigen Hapten-1-BSA was emulsified in Freund's complete adjuvant, and then the mice were immunized subcutaneously by injecting at multiple sites in the cervical-dorsal region. Four weeks after the primary immunization, the $2^{nd}$, $3^{rd}$, and $4^{th}$ immunizations were performed every 3 weeks, during which the synthetic complete antigen Hapten-1-BSA was emulsified in Freund's complete adjuvant. One week after each of the first 3 immunizations, blood was sampled from the tail vein, and the serum was separated. The serum antibody titers of the mice were monitored by indirect ELISA. One week after the $4^{th}$ immunization, blood was sampled from the tail vein, and the serum was separated. The serum antibody titers of the mice were monitored by indirect ELISA, and the serum sensitivity of the mice was measured by indirect competitive ELISA. Corresponding mice with high serum antibody titer and sensitivity were boosted for the last time. Three days before fusion, 200 µg of the immunogen was dissolved in 200 µl, of normal saline and directly intraperitoneally injected without emulsification.

Etofenprox, permethrin, and phenothrin were purchased from Sigma-Aldrich.

2. Cell Fusion

Three days after the last boost immunization, cell fusion was carried out by a conventional method using 50% by weight of polyethylene glycol (molecular weight: 1450) as a fusion agent. The steps were specifically as follows.

The mice were sacrificed by cervical dislocation and the spleens were removed under aseptic conditions. The spleen cells were isolated and mixed with murine myeloma cells SP2/0 at a ratio of 5:1. The mixed cells were washed with RPMI-1640 basal medium, and then fused with 50% PEG for 1 min. It was then top up with RPMI-1640 basal medium, and centrifuged. The supernatant was removed, and the fusion cells formed with mouse spleen cells and murine myeloma cells SP2/0 were re-suspended in 72 mL of RPMI-1640 basal medium. The re-suspended cells were added dropwise to a 96-well cell culture plate in an amount of 2 drops/well, and cultured in a $CO_2$ incubator at 37° C. The RPMI-1640 basal medium was a medium containing 20% (vol/vol) fetal bovine serum, 2% by weight (wt %) growth factor, and 1 wt % hypoxanthine-aminopterin-thymidine.

The above SP2/0 cells were purchased from Shanghai Panke Biotechnology Co., Ltd.; the RPMI-1640 basal medium was purchased from Hyclone; and the 1% hypoxanthine-aminopterin-thymidine (HAT) was purchased from Sigma-Aldrich.

3. Screening and Cloning of Cell Lines

To screen the target positive hybridoma cell line that is a highly specific and sensitive cell line against pyrethroid containing a diphenyl ether structure (by screening with etofenprox standard), the traditional two-step screening method was modified in this experiment. A gradient screening method was used in the indirect competitive ELISA screening process. (1) In the first step, an indirect non-competitive ELISA was used to screen the positive wells that recognized the diphenyl ether structure, but not the carrier protein (BSA). (2) In the second step, gradient screening was adopted for the indirect competitive ELISA; and the detection after the first subcloning was carried out by using 5 µg/mL etofenprox standard, the detection after the second subcloning was carried out by using 2 µg/mL etofenprox standard, and the detection after the third subcloning was carried out by using 1 µg/mL etofenprox standard. The positive wells with relatively small $B/B_0$ were selected, where B is the absorbance in the control well without etofenprox standard, and $B_0$ is the absorbance in the wells with etofenprox standard. The cells were cloned by limiting dilution, and detected about 10 days after the cloning by using the same two-step method as described above. After repeated cloning for 2-3 times, the hybridoma cell line QW8# was obtained.

Sequencing of Antibody Variable Region in Hybridoma Cell Line QW8# Secreting Universal Monoclonal Antibody Against Type I Pyrethroid (1) Total RNA extraction: The total RNA was extracted from the hybridoma cell line QW8# by using the total RNA extraction kit from Tiangen Biotech Co., Ltd according to the manufacturer's protocol.

(2) Synthesis of cDNA: Using the total RNA obtained in Step 1 as a template and oligo(dT)$_{15}$ as a primer, reverse transcription was performed following the instructions of SuperScript™-2II reverse transcriptase to synthesize first strand cDNA, where the primer oligo(dT)$_{15}$ was purchased from Invitrogen.

(3) Cloning of the variable region gene by PCR: Primers were designed according to the conserved sites in the mouse antibody genes in Genbank, and cDNA was used as a template to amplify the antibody heavy chain and light chain variable region genes. PCR program: 30 cycles of 30 s at 94° C., 50 s at 55° C., and 1 min at 70° C., followed by final extension for 10 min at 72° C. After the PCR product was separated by 1% (by weight) agarose gel electrophoresis, the DNA fragment was purified with a kit, ligated into the vector pMD18-T and transformed into *E. coli* DH5α competent cells. Positive clones were picked up and shipped to Suzhou Synbio Technologies Co., Ltd. for sequencing. The primer sequences were: primers for heavy chain variable region: 5'-AAGCAGTGGTATCAACGCAGAGTACATGGGG-3' (31mer) (forward primer, SEQ ID NO:5) and 5'-CAGGGGCCAGTGGATAGACAG-3' (21mer) (reverse primer, SEQ ID NO:6), and primers for light chain variable region: 5'-GCAGTGGTATCAACGCAGAGTA-CATGGGGG-3' (30mer) (forward primer, SEQ ID NO:7) and 5'-CTAAGCCTGACTGATGGCGAAG-3' (22mer) (reverse primer, SEQ ID NO:8).

Gene sequencing results: The gene sequence encoding the heavy chain variable region is 363 bp long, and is as shown in SEQ ID NO: 1. It is deduced from the gene sequence obtained that the heavy chain variable region encoded by the gene sequence consists of 121 amino acids and has a sequence as shown in SEQ ID NO: 3. The gene sequence encoding the light chain variable region is 327 bp long and is as shown in SEQ ID NO: 2. It is deduced from the gene sequence obtained that the light chain variable region encoded by the gene sequence consists of 109 amino acids, and has a sequence as shown in SEQ ID NO: 4.

Preparation, Purification, Subtyping, and Characteristic Determination of Universal Monoclonal Antibody Against Type I Pyrethroid BALB/c mice previously treated with incomplete Freund's adjuvant were injected with the obtained hybridoma cell line QW8# secreting universal monoclonal antibody against pyrethroid type I. The ascetic fluid of the mice was collected and the antibody was purified by caprylic acid/ammonium sulfate precipitation. The process was specifically as follows. The ascetic fluid was taken out from a freezer at −20° C. and thawed at room temperature. The ascetic fluid was filtered through double-layered filter paper to preliminarily remove the fatty pieces, cell debris and other impurities. The ascetic fluid was centrifuged for 15 min at 12000 revolutions per min, the supernatant was collected and the pellet was discarded. The volume of the ascetic fluid was accurately measured. One volume of the ascetic fluid and 3 volumes of an acetate buffer were well mixed by magnetic stirring, and adjusted to pH 4.5-4.8 with 2 mol/L HCl. During stirring, n-octanoic acid was slowly added in an amount of 33 μL of n-octanoic acid per 1 mL of ascetic fluid, magnetically stirred for half an hour at room temperature, and then allowed to stand at 4° C. for 2 hours. Then the mixture was centrifuged for 5 min at 12000 revolutions per min. The supernatant was collected and filtered through double-layered filter paper, and the filtrate was collected. The volume of the filtrate was measured, 1/10 volume of 0.1 M PBS (pH 7.4) was added, and the resulting mixture was adjusted to pH 7.4 with 2 mol/L NaOH (where the NaOH volume was recorded). The supernatant was pre-cooled in an ice bath, and solid ammonium sulfate was added in 30 min with stirring to give a concentration of 0.277 g/mL and then allowed to stand overnight at 4° C. The liquid was centrifuged for 15 min at 12000 revolutions per min, and the supernatant was discarded. The pellet was dissolved with a volume of 0.01 mol/L PBS. After dialysis for two days in 0.01 mol/L PBS, the dialysate was collected, and centrifuged for 15 min at 12000 revolutions per min. The supernatant was collected, pre-frozen at −20° C., and then freeze-dried under vacuum into a powder for storage.

The acetate buffer contained 0.29 g sodium acetate, 0.141 mL acetic acid and water q.s. to 100 mL. The 0.1 mol/L phosphate buffer contained 0.8 g sodium chloride, 0.29 g disodium hydrogen phosphate dodecahydrate, 0.02 g potassium chloride, 0.02 g potassium dihydrogen phosphate, and water q.s. to 100 mL.

The universal monoclonal antibody against type I pyrethroid secreted by hybridoma cell line QW8# was identified to be subtype IgG2a by using a commercial subtype identification kit.

The affinity for QW8# was determined by indirect non-competitive ELISA. The plate was coated at 37° C. for 2 hours with Hapten-1-BSA at concentrations of 2.0, 1.0, 0.5, and 0.25 μg/mL in an amount of 100 μL/well. After the plate was blocked with a blocking solution for 1 hour, the antibody diluted with PBS (at a dilution factor of 1:2) was added to the plate and the rest steps were the same as those in indirect non-competitive ELISA. The $OD_{450}$ values measured was used as the vertical coordinates, the values of the logarithm of the antibody concentrations (mol/L) were used as the horizontal coordinates, 4 S-shaped curves corresponding to the 4 concentrations were plotted. The maximum OD value ($OD_{max}$) at the top of each S-curve, that is, the concentration of the antibody that corresponds to 50% of the $OD_{max}$, was obtained from each curve. The 4 concentrations were paired, and the affinity constant ($K_a$) of the antibody was calculated by using the formula $K_a=(n-1)/2(n[Ab']t-[Ab]t)$, where [Ab']t, and [Ab]t are antibody concentrations corresponding to 50% of two $OD_{max}$ values in each group, and n is the multiple of the antigen concentration coated in each group. The affinity of the antibody against type I pyrethroid derived from mouse ascetic fluid is $2.16\times10^8$ L/mol by enzyme-linked immunosorbent assay (ELISA). The $IC_{50}$ value of the universal monoclonal antibody against pyrethroid is 20.86 μg/L for etofenprox and the minimum detectable limit is 3.16 μg/L by conventional indirect competitive ELISA. The $IC_{50}$ value for permethrin is 24.2 μg/L, and the minimum detectable limit is 3.72 μg/L. The $IC_{50}$ value for phenothrin is 29.4 n/L and the minimum detectable limit is 4.27 μg/L. The cross-reactivity with other type I and type II pyrethroids is less than 1%.

Example 2: Rapid Time-Resolved Fluorescent Immunochromatographic Assay Kit for Type I Pyrethroid and its Application A time-resolved fluorescent immunochromatographic assay rapid test kit for type I pyrethroid comprises a fluorescent test strip, a sample reaction vial containing a lyophilized product of a europium-labelled universal monoclonal antibody against type I pyrethroid, a sample diluent, and a sample dilution pipette. The fluorescent test strip comprises a cardboard comprising an absorbent pad, a detection pad, and a sample pad adhered in sequence from top to bottom on one side, in which the adjacent pads are connected at an overlapped junction over a length of 1 mm. The absorbent pad is 15 mm long and 4 mm wide; the detection pad is 25 mm long and 4 mm wide; and the sample pad is 13 mm long and 4 mm wide. The detection pad comprises a nitrocellulose membrane as a base pad, and transverse quality control line and detection line are arranged on the nitrocellulose membrane from top to bottom. The quality control line is coated with rabbit anti-mouse polyclonal antibody, and the detection line is coated with a complete antigen of type I pyrethroid. The detection line is 15 mm away from a top edge of the nitrocellulose membrane, and the distance between the quality control line and the detection line is 5 mm.

The fluorescent test strip was obtained through a process comprising the following steps.

(1) Preparation of Absorbent Pad

Absorbent paper was cut to obtain an absorbent pad having a length of 15 mm and a width of 4 mm.

(2) Preparation of Detection Pad

Coating of Detection Line:

The complete antigen (hapten-1-OVA) of type I pyrethroid was formulated into a 0.8 mg/mL coating solution in a coating buffer. The coating solution was transversely coated on a nitrocellulose membrane by means of line spray at a position that was 15 mm away from a top edge of the nitrocellulose membrane, to obtain a detection line. The hapten-1-OVA was coated in an amount of 480 ng/cm of the detection line. Then, the coating solution was dried for 30 min at 37° C.

The coating buffer contained 0.1 g bovine serum albumin, 0.002 g sodium azide, 0.08 g sodium chloride, 0.029 g disodium hydrogen phosphate dodecahydrate, 0.002 g potassium chloride, 0.002 g potassium dihydrogen phosphate, and water q.s. to 10 mL.

Coating of Quality Control Line:

The rabbit anti-mouse polyclonal antibody was formulated into a 0.25 mg/mL coating solution in a coating buffer. The coating solution was transversely coated on the nitrocellulose membrane by means of line spray at a position that was 6 mm away from the detection line, to obtain a quality control line. The rabbit anti-mouse polyclonal antibody was coated in an amount of 100 ng/cm of the quality control line. Then, the coating solution was dried for 1 hour at 37° C.

The coating buffer contained 0.002 g sodium azide, 0.08 g sodium chloride, 0.029 g disodium hydrogen phosphate dodecahydrate, 0.002 g potassium chloride, 0.002 g potassium dihydrogen phosphate, and water q.s. to 10 mL.

(3) Preparation of Sample Pad:

A glass fiber membrane was cut to have a size of 13 mm in length and 4 mm in width, soaked in a blocking solution, taken out, and dried for 6 hours at 37° C., to obtain a sample pad, which was then stored in desiccator at room temperature.

The blocking solution contained 1 g ovalbumin, 2 g sucrose, 0.02 g sodium azide, 0.8 g sodium chloride, 0.29 g disodium hydrogen phosphate dodecahydrate, 0.02 g potassium chloride, 0.02 g potassium dihydrogen phosphate, and water q.s. to 100 mL.

Figure 2:
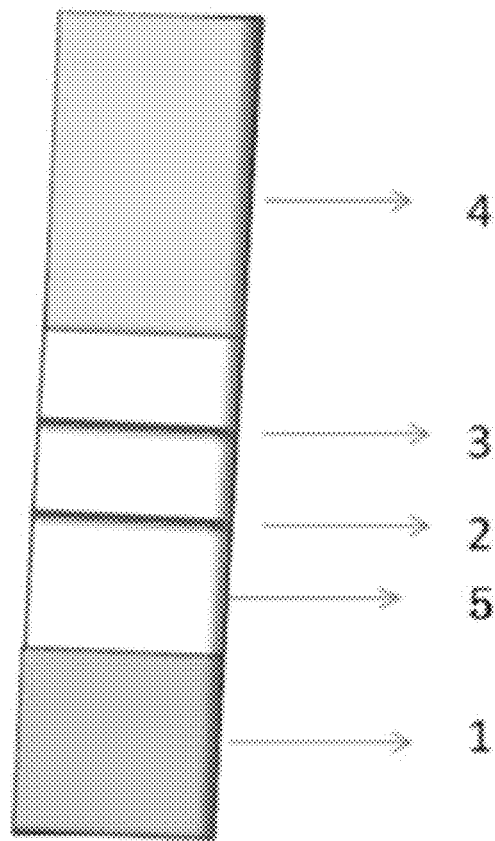
FIG. 2 is a schematic structural diagram of a fluorescent test strip in a time-resolved fluorescent immunochromatographic assay rapid test kit for type I pyrethroid provided in the present invention, comprising sample pad 1, detection line 2, quality control line 3, absorbent pad 4, and detection pad 5.

(4) Assembly of Fluorescent Test Strip:

The absorbent pad, the detection pad, a fluorescently labelled antibody reaction pad, and the sample pad were adhered in sequence from top to bottom on one side of a cardboard, in which the adjacent pads were folded at the connections over a length of 2 mm, to obtain a fluorescent test strip (as shown in FIG. 2).

The europium-labelled universal monoclonal antibody against type I pyrethroid was obtained through a process comprising the following.

1 mg of the universal monoclonal antibody was repeatedly washed 6 time with a 100 mmol/L carbonate buffer (pH 9.3), mixed uniformly with 2 mg of a europium labelling reagent, and allowed to stand overnight at 4° C. Then, the resulting mixture was loaded onto a SEPHADEX® G-50 chromatographic column of 1.9 cm×60 cm, and eluted with an eluant containing 0.9% NaCl in 50 mmol/L Tris-HCl. The effluent was collected (1 mL/tube), and the absorbance at 280 nm ($A_{280}$) was measured for each tube. The peak tubes were combined, to obtain the target product europium-labelled universal monoclonal antibody against type I pyrethroid. The europium labelling reagent was purchased from Shanghai Uni Biotech. Co., Ltd, without limitation.

The sample reaction vial containing a lyophilized product of a europium-labelled universal monoclonal antibody against type I pyrethroid was obtained as follows. 0.25 μg of the europium-labelled universal monoclonal antibody against type I pyrethroid was placed in a 3-mL bayonet vial, and dried by conventional freeze-drying under vacuum, to obtain a lyophilized powder of europium-labelled universal monoclonal antibody against type I pyrethroid, which was stored at 4° C. for later use.

Use of the Time-Resolved Fluorescent Immunochromatographic Assay Rapid Test Kit in the Detection of Type I Pyrethroid in Chinese Cabbage Sample Establishment of relation curve of ratio of fluorescence intensity of detection line to fluorescence intensity of quality control line on fluorescent test strip (T/C) against concentration of type I pyrethroid:

(1) Chinese cabbage samples that were detected to be etofenprox, permethrin and phenothrin negative by high performance liquid chromatography (HPLC) were pretreated. Etofenprox, permethrin and phenothrin were added at a ratio of 1:1:1 to obtain standard solutions having a concentration of 10 μg/mL, 5 μg/mL, 2 μg/mL, 1 μg/mL, 0.5 μg/mL, 0.2 μg/mL, 0.1 ng/mL, 0.05 μg/mL, 0.02 μg/mL, and 0.01 μg/mL.

(2) Each 100 μL of the various concentrations of type I pyrethroid standard solution was respectively added to a sample reaction vial, and mixed uniformly. Then a fluorescent test strip was added, and reacted for 6 min at 37° C. Remaining liquid on the sample pad was absorbed by absorbent paper and then detected by using a time-resolved fluorescent immunochromatographic assay instrument (at an excitation wavelength of 365 nm and a detection wavelength of 615 nm) immediately, to obtain fluorescence intensity values of the detection line (T) and the quality control line (C) on each fluorescent test strip. Thus, the ratio (T/C) of the fluorescence intensity of the detection line to the fluorescence intensity of the quality control line on each fluorescent test strip was obtained.

(3) A standard curve was established with the standard concentrations as horizontal coordinates and T/C values as longitudinal coordinates. The quantitative detection limit was 9.12 ng/mL.

(4) Etofenprox, permethrin, and phenothrin were mixed and added to blank Chinese cabbage sample to give a standard concentration of 2 μg/mL, 0.1 μg/mL, and 0.01 μg/mL. The concentration of type I pyrethroid measured by the fluorescent test strip is used as a horizontal coordinate, the concentration of type I pyrethroid measured by HPLC is used as a longitudinal coordinate, and the recovery rate in the method ranges from 90.4% to 118.1%.

Example 3: Time-Resolved Fluorescent Immunochromatographic Assay Rapid Test Kit for Type I Pyrethroid and Use Thereof A time-resolved fluorescent immunochromatographic assay rapid test kit for type I pyrethroid comprises a fluorescent test strip, a sample reaction vial containing a lyophilized product of a europium-labelled universal monoclonal antibody against type I pyrethroid, a sample diluent, and a sample dilution pipette. The fluorescent test strip comprises a cardboard comprising an absorbent pad, a detection pad, and a sample pad adhered in sequence from top to bottom on one side, in which the adjacent pads are folded at the connections over a length of 1 mm. The absorbent pad was 18 mm long and 3 mm wide; the detection pad was 28 mm long and 3 mm wide; and the sample pad was 15 mm long and 3 mm wide. The detection pad comprises a nitrocellulose membrane as a base pad, and transverse quality control line and detection line are arranged on the nitrocellulose membrane from top to bottom. The quality control line is coated with rabbit anti-mouse polyclonal antibody in an amount of 150 ng/cm quality control line, and the detection line is coated with a complete antigen (hapten-1-OVA) of type I pyrethroid in an amount of 550 ng/cm detection line. The detection line is 20 mm away from a top edge of the nitrocellulose membrane, and the distance between the quality control line and the detection line is 10 mm.

The fluorescent test strip was obtained through a process comprising the following steps.

(1) Preparation of Absorbent Pad

Absorbent paper was cut to obtain an absorbent pad having a length of 18 mm and a width of 3 mm.

(2) Preparation of Detection Pad

Coating of Detection Line:

The complete antigen (hapten-1-OVA) of type I pyrethroid (etofenprox) was formulated into a 0.8 ng/mL coating solution in a coating buffer. The coating solution was transversely coated on a nitrocellulose membrane by means of line spray at a position that was 20 mm away from a top edge of the nitrocellulose membrane, to obtain a detection line. The complete antigen (hapten-1-OVA) of type I pyrethroid (etofenprox) was coated in an amount of 480 ng/cm of the detection line. Then, the coating solution was dried for 30 min at 40° C.

The coating buffer contained 0.1 g bovine serum albumin, 0.002 g sodium azide, 0.08 g sodium chloride, 0.029 g disodium hydrogen phosphate dodecahydrate, 0.002 g potassium chloride, 0.002 g potassium dihydrogen phosphate, and water q.s. to 10 mL.

Coating of Quality Control Line:

The rabbit anti-mouse polyclonal antibody was formulated into a 0.25 mg/mL coating solution in a coating buffer. The coating solution was transversely coated on the nitrocellulose membrane by means of line spray at a position that was 6 mm away from the detection line, to obtain a quality control line. The rabbit anti-mouse polyclonal antibody was coated in an amount of 100 ng/cm of the quality control line. Then, the coating solution was dried for 30 min at 40° C.

The coating buffer contained 0.002 g sodium azide, 0.08 g sodium chloride, 0.029 g disodium hydrogen phosphate dodecahydrate, 0.002 g potassium chloride, 0.002 g potassium dihydrogen phosphate, and water q.s. to 10 mL.

The nitrocellulose membrane was 28 mm long and 3 mm wide.

(3) Preparation of Sample Pad:

A glass fiber membrane was cut to have a size of 15 mm in length and 3 mm in width, soaked in a blocking solution, taken out, and dried for 6 hours at 37° C., to obtain a sample pad, which was then stored in desiccator at room temperature.

The blocking solution contained 1 g ovalbumin, 2 g sucrose, 0.02 g sodium azide, 0.8 g sodium chloride, 0.29 g disodium hydrogen phosphate dodecahydrate, 0.02 g potassium chloride, 0.02 g potassium dihydrogen phosphate, and water q.s. to 100 mL.

(4) Assembly of Fluorescent Test Strip:

The absorbent pad, the nitrocellulose membrane and the sample pad were adhered in sequence from top to bottom on one side of a cardboard, in which the adjacent pads were connected at the overlapped junction of the adjacent pads over a length of 2 mm, to obtain a fluorescent test strip.

The europium-labelled universal monoclonal antibody against type I pyrethroid was obtained through a process comprising the following.

1 mg of the universal monoclonal antibody in Example 3 was repeatedly washed 6 time with a 100 mmol/L carbonate buffer (pH 9.3), mixed uniformly with 2 mg of a europium labelling reagent, and allowed to stand overnight at 4° C. Then, the resulting mixture was loaded onto a SEPHADEX® G-50 chromatographic column of 1.9 cm×60 cm, and eluted with an eluant containing 0.9% NaCl in 50 mmol/L Tris-HCl. The effluent was collected (1 ml/tube), and the absorbance at 280 nm ($A_{280}$) was measured for each tube. The peak tubes were combined, to obtain the target product europium-labelled universal monoclonal antibody against type I pyrethroid. The europium labelling reagent was purchased from Shanghai Uni Biotech. Co., Ltd, without limitation.

The sample reaction vial containing a lyophilized product of a europium-labelled universal monoclonal antibody against type I pyrethroid was obtained as follows. 0.25 μg of the europium-labelled universal monoclonal antibody against type I pyrethroid was placed in a 3-mL bayonet vial, and dried by conventional freeze-drying under vacuum, to obtain a lyophilized powder of europium-labelled universal monoclonal antibody against type I pyrethroid, which was stored at 4° C. for later use.

The sample diluent was a 0.30% (vol/vol) solution of TWEEN®20 (polyoxyethylene (20) sorbitan monolaurate) in water.

Use of the Time-Resolved Fluorescent Immunochromatographic Assay Rapid Test Kit in the Detection of Type I Pyrethroid in Chinese Cabbage Sample Five Chinese cabbage samples were taken and pretreated. Each 200 μL was added to a sample reaction vial, and mixed until uniform. Then a fluorescent test strip was added, and reacted for 6 min at 37° C. Remaining liquid on the sample pad was absorbed by absorbent paper and then detected by using a time-resolved fluorescent immunochromatographic assay instrument (at an excitation wavelength of 365 nm and a detection wavelength of 615 nm) immediately, to obtain a ratio of the fluorescence intensity of the detection line and the fluorescence intensity of the quality control line (T/C) on each fluorescent test strip. Then, the value was inserted into a relation curve of the ratio of the fluorescence intensity of the detection line to the fluorescence intensity of the quality control line on the fluorescent test strip (T/C) against the concentration of type I pyrethroid. The recovery rate in the detection ranges from 94.48% to 112.2%, and the coefficient of correlation between the detection results obtained with the kit and by HPLC is 0.986 ($R^2$).

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A time-resolved fluorescent immunochromatographic assay rapid test kit for type I pyrethroid, comprising a fluorescent test strip, and a sample reaction vial containing a lyophilized product of an europium-labelled universal monoclonal antibody against type I pyrethroid, wherein the fluorescent test strip comprises a cardboard, the cardboard comprises a plurality of adjacent pads comprising an absorbent pad, a detection pad, and a sample pad adhered in sequence from top to bottom on one side of the cardboard, wherein each of the plurality of adjacent pads are connected at an overlapped junction of the plurality of adjacent pads; the detection pad comprises a nitrocellulose membrane as a base pad, a transverse quality control line and a detection line are arranged from top to bottom on the nitrocellulose membrane, the quality control line is coated with a rabbit anti-mouse polyclonal antibody, and the detection line is coated with a complete antigen of type I pyrethroid; and the universal monoclonal antibody against type I pyrethroid is produced from a hybridoma cell line QW8#, deposited on Aug. 30, 2016 to China Center for Type Culture Collection (CCTCC) in Wuhan University, Wuhan, China under CCTCC Accession No. of C2016164.

2. The time-resolved fluorescent immunochromatographic assay rapid test kit for type I pyrethroid according to claim 1, wherein the complete antigen of type I pyrethroid comprises a structural formula of:

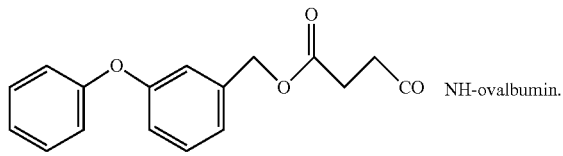

3. The time-resolved fluorescent immunochromatographic assay rapid test kit for type I pyrethroid according to claim 1, wherein the europium-labelled universal monoclonal antibody against type I pyrethroid is prepared through a process comprising: dialyzing the universal monoclonal antibody against type I pyrethroid in a carbonate buffer solution, mixing fully with an europium labelling reagent at a weight ratio of 0.5-2:1, allowing the mixture to stand overnight, and then separating the europium-labelled universal monoclonal antibody against type I pyrethroid by chromatography using G-50 chromatographic column, followed by elution, and collection of targeted product.

4. The time-resolved fluorescent immunochromatographic assay rapid test kit for type I pyrethroid according to claim 1, wherein in the fluorescent test strip, the absorbent pad is 15-20 mm long and 3-4 mm wide; the detection pad is 25-30 mm long and 3-4 mm wide; the sample pad is 12-18 mm long and 3-4 mm wide; the overlapped junction of the plurality of adjacent pads is 1-3 mm long; and
the detection line on the detection pad in the fluorescent test strip is 15-20 mm away from a top edge of the nitrocellulose membrane; the distance between the quality control line and the detection line is 5-10 mm; and the sample reaction vial is a 1-5 mL bayonet vial.

5. The time-resolved fluorescent immunochromatographic assay rapid test kit for type I pyrethroid according to claim 1, wherein the complete antigen of type I pyrethroid is coated in an amount of 480-1000 ng/cm on the detection line of the detection pad in the fluorescent test strip; the rabbit anti-mouse polyclonal antibody is coated in an amount of 100-900 ng/cm on the quality control line; and the content of the lyophilized product of the europium-labelled universal monoclonal antibody against type I pyrethroid in the sample reaction vial is 0.2-1.0 µg.

6. The time-resolved fluorescent immunochromatographic assay rapid test kit for type I pyrethroid according to claim 1, wherein the fluorescent test strip is prepared through a process comprising steps of:
(1) cutting an absorbent paper to obtain the absorbent pad;
(2) preparation of the detection pad, comprising:
formulating a coating solution of the complete antigen of type I pyrethroid into a concentration of 0.2-1.0 mg/mL, coating transversely on a nitrocellulose membrane by means of line spray to obtain the detection line, and then drying for 30-60 min at 37-40° C.; and
formulating a coating solution of the rabbit anti-mouse polyclonal antibody into a concentration of 0.10-0.80 mg/mL, coating transversely on the nitrocellulose membrane by means of line spray to obtain the quality control line, and then drying for 30-60 min at 37-40° C.;
(3) preparation of the sample pad, comprising
soaking a glass fiber membrane in a blocking solution, taking out, and drying for 3-6 hours at 37-40° C., to obtain the sample pad, which is then stored in a desiccator at room temperature; and
(4) assembly of the fluorescent test strip, comprising
adhering the plurality of adjacent pads comprising the absorbent pad, the detection pad, and the sample pad from top to bottom on one side of the cardboard, wherein each of the plurality of adjacent pads are connected at the overlapped junction of the plurality of adjacent pads to obtain the fluorescent test strip.

7. The time-resolved fluorescent immunochromatographic assay rapid test kit for type I pyrethroid according to claim 6, wherein in the preparation of the fluorescent test strip,
the coating solution of the complete antigen of type I pyrethroid is formulated in a coating buffer comprising 0.1 g bovine serum albumin, 0.002 g sodium azide, 0.08 g sodium chloride, 0.029 g disodium hydrogen phosphate dodecahydrate, 0.002 g potassium chloride, and 0.002 g potassium dihydrogen phosphate per 10 mL; and
the coating solution of the rabbit anti-mouse polyclonal antibody is formulated in a coating buffer comprising 0.002 g sodium azide, 0.08 g sodium chloride, 0.029 g disodium hydrogen phosphate dodecahydrate, 0.002 g potassium chloride, and 0.002 g potassium dihydrogen phosphate per 10 mL; and
the blocking solution used in the preparation of the fluorescent test strip comprises 0.5-2 g ovalbumin, 2 g sucrose, 0.02 g sodium azide, 0.8 g sodium chloride, 0.29 g disodium hydrogen phosphate dodecahydrate, 0.02 g potassium chloride, and 0.02 g potassium dihydrogen phosphate per 100 mL.

8. The time-resolved fluorescent immunochromatographic assay rapid test kit for type I pyrethroid according to claim 1, further comprising a sample diluent, and a sample dilution pipette, wherein the sample diluent is a solution with 0.01-0.30% (vol/vol) of polyoxyethylene (20) sorbitan monolaurate in water.

9. A method of determining a concentration of type I pyrethroid using the time-resolved fluorescent immunochromatographic assay rapid test kit for type I pyrethroid according to claim 1, comprising adding a sample solution to be tested to the sample reaction vial, mixing fully, inserting the fluorescent test strip into the sample solution to be tested, reacting for 6 min at 37° C., and assaying by using a time-resolved fluorescent immunochromatographic assay instrument, to obtain a relation curve of a ratio of a fluorescence intensity value of the detection line (T) to a fluorescence intensity value of the quality control line (C) on the fluorescent test strip (T/C); and obtaining the concentration of type I pyrethroid in the sample solution to be tested, according to the previously obtained relation curve of the ratio of the fluorescence intensity of the detection line (T) to the fluorescence intensity of the quality control line (C) on the fluorescent test strip (T/C) against the concentration of type I pyrethroid.

10. The method of determining a concentration of type I pyrethroid using the time-resolved fluorescent immunochromatographic assay rapid test kit for type I pyrethroid according to claim 9, wherein the relation curve of the ratio of the fluorescence intensity of the detection line (T) to the fluorescence intensity of the quality control line (C) on the fluorescent test strip (T/C) against the concentration of type I pyrethroid is obtained by steps comprising:

(1) formulating a standard solution comprising a series of concentrations of type I pyrethroid;

(2) adding a suitable amount of the standard solution comprising the series of concentrations of type I pyrethroid respectively to a sample reaction vial, mixing fully, inserting fluorescent test strips into the standard solution, reacting for 6 min at 37° C., assaying by using a time-resolved fluorescent immunochromatographic assay instrument, to obtain fluorescence intensity values of the detection line (T) and the quality control line (C) on each of the fluorescent test strips, and obtaining a ratio of the fluorescence intensity values of the detection line (T) and the quality control line (C) on each of the fluorescent test strips (T/C); and (3) fitting to obtain the relation curve of the ratio of the fluorescence intensity of the detection line (T) to the fluorescence intensity of the quality control line (C) on the fluorescent test strip (T/C) against the concentration of type I pyrethroid.

* * * * *